US 11,424,775 B2

(12) United States Patent
Oh et al.

(10) Patent No.: US 11,424,775 B2
(45) Date of Patent: Aug. 23, 2022

(54) HUMAN BODY COMMUNICATION RECEIVER AND OPERATING METHOD THEREOF

(71) Applicant: ELECTRONICS AND TELECOMMUNICATIONS RESEARCH INSTITUTE, Daejeon (KR)

(72) Inventors: Kwang Il Oh, Daejeon (KR); Tae Wook Kang, Daejeon (KR); Sung Eun Kim, Daejeon (KR); Hyuk Kim, Daejeon (KR); Hyung-Il Park, Daejeon (KR); Kyung Jin Byun, Daejeon (KR); Jae-Jin Lee, Daejeon (KR); In Gi Lim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 17/237,848

(22) Filed: Apr. 22, 2021

(65) Prior Publication Data
US 2021/0384929 A1    Dec. 9, 2021

(30) Foreign Application Priority Data

Jun. 3, 2020  (KR) ................. 10-2020-0066953
Oct. 12, 2020 (KR) ................. 10-2020-0130978

(51) Int. Cl.
*H04B 1/10* (2006.01)
*H04B 1/16* (2006.01)
(Continued)

(52) U.S. Cl.
CPC .............. *H04B 1/10* (2013.01); *A61N 1/025* (2013.01); *H03K 3/013* (2013.01); *H04B 1/1607* (2013.01); *H04B 13/00* (2013.01); *G01R 13/00* (2013.01)

(58) Field of Classification Search
CPC ........ H04B 1/10; H04B 1/1607; H04B 13/00; A61N 1/025; H03K 3/013; G01R 13/00
See application file for complete search history.

(56) References Cited

U.S. PATENT DOCUMENTS 8,320,429 B2   11/2012  Kang et al.
8,472,501 B2    6/2013  Lim et al.
(Continued)

FOREIGN PATENT DOCUMENTS

CN       110677216 A     1/2020
JP      2014045393 A     3/2014
(Continued)

*Primary Examiner* — Janice N Tieu (57) ABSTRACT

Disclosed are a human body communication receiver and an operating method thereof, which may effectively remove low frequency noise. The human body communication receiver according to the present disclosure includes a receiving electrode, a virtual electrode, a filter circuit that is connected between the receiving electrode and the virtual electrode, and removes low frequency noise from a signal received through the receiving electrode to generate a high frequency signal, a low frequency reconstruction circuit that is connected to a rear end of the filter circuit and reconstructs a low frequency baseband signal by rectifying the high frequency signal, and an amplifying circuit that is connected to a rear end of the low frequency reconstruction circuit, and amplifies the low frequency baseband signal.

14 Claims, 6 Drawing Sheets

(51) Int. Cl.
  *A61N 1/02*  (2006.01)
  *H03K 3/013*  (2006.01)
  *H04B 13/00*  (2006.01)
  *G01R 13/00*  (2006.01)

(56) References Cited

U.S. PATENT DOCUMENTS

| | | |
|---|---|---|
| 8,798,049 B2 | 8/2014 | Lim et al. |
| 2005/0117502 A1* | 6/2005 | Kanda ............... G11B 7/005 |
| | | 369/124.11 |
| 2009/0086864 A1* | 4/2009 | Komninakis ............ H04B 1/10 |
| | | 455/296 |
| 2010/0137708 A1* | 6/2010 | Tamura ................. A61B 5/053 |
| | | 600/424 |
| 2014/0348270 A1* | 11/2014 | Babu ..................... H04B 13/00 |
| | | 375/317 |
| 2017/0207861 A1 | 7/2017 | Hyoung |
| 2018/0178059 A1* | 6/2018 | Kim .................. A63B 24/0087 |
| 2020/0259569 A1* | 8/2020 | Oh .......................... H03F 3/245 |

FOREIGN PATENT DOCUMENTS

| | | |
|---|---|---|
| KR | 20090128305 A | 12/2009 |
| KR | 201 00045126 A | 5/2010 |
| KR | 201 00120042 A | 11/2010 |
| KR | 20180059721 A | 6/2018 |

\* cited by examiner

HUMAN BODY COMMUNICATION RECEIVER AND OPERATING METHOD THEREOF

CROSS-REFERENCE TO RELATED APPLICATIONS

This application claims priority under 35 U.S.C. § 119 to Korean Patent Application Nos. 10-2020-0066953, filed on Jun. 3, 2020, and 10-2020-0130978, filed on October 12, respectively, in the Korean Intellectual Property Office, the disclosures of which are incorporated by reference herein in their entireties.

BACKGROUND

Embodiments of the present disclosure described herein relate to a human body communication receiver, and more particularly, relate to a human body communication receiver capable of effectively removing low frequency noise and a method of operating the same.

Human body communication is one of communication methods for transmitting signals and information from a transmitter to a receiver using a human body as a medium. Since the signals are transmitted through the human body rather than radiating information into an air like wireless communication, the human body communication has a binding force on the signals. Therefore, as digital signals may be directly transmitted to and received from the human body without the need for modulation and demodulation of the signals, the human body communication has a relatively simple structure and low power consumption.

A band pass filter is provided for filtering signals in unnecessary signal bands other than a signal band transmitted by the transmitter, among the signals received by the human body communication receiver. To effectively complete the band pass, it is very important to implement an optimal filter structure for signal integrity.

SUMMARY

Embodiments of the present disclosure provide a human body communication receiver including a low frequency reconstruction circuit that reconstructs a high frequency signal obtained by removing low frequency noise from a reception signal into an original low frequency baseband signal, and a method of operating the same.

According to an embodiment of the present disclosure, a human body communication receiver includes a receiving electrode, a virtual electrode, a filter circuit that is connected between the receiving electrode and the virtual electrode, and removes low frequency noise from a signal received through the receiving electrode to generate a high frequency signal, a low frequency reconstruction circuit that is connected to a rear end of the filter circuit and reconstructs a low frequency baseband signal by rectifying the high frequency signal, and an amplifying circuit that is connected to a rear end of the low frequency reconstruction circuit, and amplifies the low frequency baseband signal.

According to an embodiment of the present disclosure, an operating method of the human body communication receiver includes removing, by a filter circuit connected between a receiving electrode and a virtual electrode, low frequency noise from a signal received through the receiving electrode, reconstructing, by a low frequency reconstruction circuit connected to a rear end of the filter circuit, a low frequency baseband signal by rectifying the high frequency signal, and amplifying, by an amplifying circuit connected to a rear end of the low frequency reconstruction circuit, the low frequency baseband signal.

BRIEF DESCRIPTION OF THE FIGURES

The above and other objects and features of the present disclosure will become apparent by describing in detail embodiments thereof with reference to the accompanying drawings.

DETAILED DESCRIPTION

Hereinafter, embodiments of the present disclosure will be described clearly and in detail such that those skilled in the art may easily carry out the present disclosure.

Components described with reference to terms such as parts or units, modules, blocks, and ~er or ~or, which are used in the detailed description and functional blocks illustrated in the drawings may be implemented in the form of software, hardware, or a combination of hardware and software. Illustratively, the software may be machine code, firmware, embedded code, or application software. For example, the hardware may include electrical circuits, electronic circuits, processors, computers, integrated circuits, integrated circuit cores, pressure sensors, inertial sensors, microelectromechanical systems (MEMS), passive elements, or combinations thereof.

Figure 1:
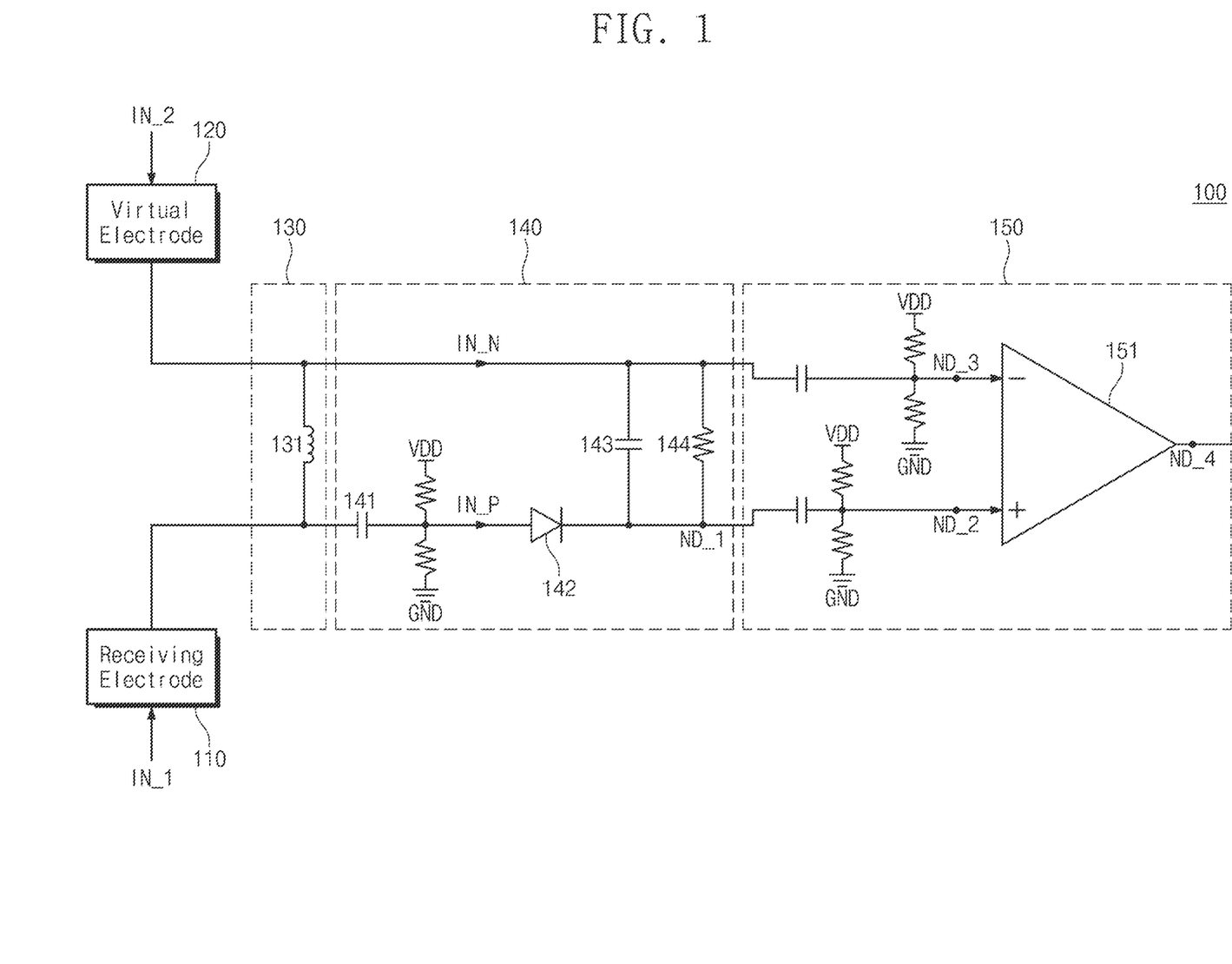
FIG. 1 is a circuit diagram illustrating a configuration of a human body communication receiver according to an embodiment of the present disclosure.

FIG. 1 is a circuit diagram illustrating a configuration of a human body communication receiver 100 according to an embodiment of the present disclosure. When the human body communication receiver 100 receives a signal (hereinafter referred to as a "transmission signal") transmitted from a human body communication transmitter (not illustrated) using a human body as a medium, the human body communication receiver 100 may remove low frequency noise included in the reception signal, and may reconstruct the signal from which the low frequency noise is removed into a low frequency baseband signal and then may amplify the reconstructed low frequency baseband signal. The human body communication receiver 100 may include a receiving electrode 110, a virtual electrode 120, a filter circuit 130, a low frequency reconstruction circuit 140, and an amplifying circuit 150.

The receiving electrode 110 may receive a first reception signal IN_1. The first reception signal IN_1 may include a transmission signal and low frequency noise introduced from noise sources (e.g., a fluorescent lamp) around the human body. For example, the transmission signal may include a high frequency pulse. For example, the receiving electrode 110 may be directly attached to an epidermis of the human body. For example, the receiving electrode 110 may be connected to a positive input of a differential amplifier 151.

The virtual electrode 120 may receive a second reception signal IN_2 that is used when the amplifying circuit 150 differentially amplifies the low frequency baseband signal. The second reception signal IN_2 may include low frequency noise introduced from the noise sources, but unlike the first reception signal IN_1, the second reception signal IN_2 may not include the transmission signal. For example, the virtual electrode 120 may be located on the opposite side of the location where the receiving electrode is attached, and the virtual electrode 120 may protrude outside the human body communication receiver 100 or may be located inside the human body communication receiver 100. For example, the virtual electrode 120 may not contact the epidermis of the human body. For example, the virtual electrode 120 may be connected to a negative input of the differential amplifier 151.

The filter circuit 130 may remove low frequency noise included in the first reception signal IN_1. The filter circuit 130 may be connected between the receiving electrode 110 and the amplifying circuit 150, and the virtual electrode 120 and the amplifying circuit 150. The filter circuit 130 may include at least one inductor 131, but the present disclosure is not limited thereto.

The impedance of the inductor 131 may be lowered in a low frequency band. Accordingly, the inductor 131 may short the receiving electrode 110 and the virtual electrode 120 such that the low frequency noise included in the first reception signal IN_1 that is input to the receiving electrode 110 may be removed. The filter circuit 130 may output a high frequency signal from which low frequency noise is removed by the inductor 131 to the low frequency reconstruction circuit 140.

As described above, the second reception signal IN_2 input to the virtual electrode 120 may not include the transmission signal, and in this case, may not include a signal of a high frequency band. Accordingly, when a signal of the low frequency band is removed from the second reception signal IN_2 by the inductor 131, a magnitude of the signal may be close to zero. The filter circuit 130 may output a negative input signal IN_N of which the magnitude is close to zero.

The low frequency reconstruction circuit 140 may reconstruct the high frequency signal from which the low frequency noise is removed into the low frequency baseband signal. The low frequency reconstruction circuit 140 may be connected between the receiving electrode 110 and the amplifying circuit 150, and between the virtual electrode 120 and the amplifying circuit 150, and may be connected to a rear end of the filter circuit 130. The low frequency reconstruction circuit 140 may include a capacitor 141 connected in series with the receiving electrode 110, a diode 142 connected in series with the capacitor 141, and a capacitor 143 and a load resistor 144 that are connected in parallel between the diode 142 and the virtual electrode 120, but the present disclosure is not limited thereto. For example, the low frequency reconstruction circuit 140 may include resistors connected between a power supply voltage VDD and a ground GND at the rear end of the capacitor 141, but the present disclosure is not limited thereto.

The low frequency reconstruction circuit 140 may receive a signal from which the low frequency noise output from the filter circuit 130 is removed. The signal from which the low frequency noise is removed may pass through the capacitor 141, and a positive input signal IN_P passing through the capacitor 141 may be input to the anode of the diode 142. Resistors connected between the power supply voltage VDD and the ground GND may apply a bias voltage to the anode of the diode 142 such that the positive input signal IN_P exceeds a threshold voltage of the diode 142.

The diode 142 may output a rectified signal obtained by rectifying the positive input signal IN_P to a cathode. The capacitor 143 may charge the rectified signal, and the rectified signal charged in the capacitor 143 may be discharged by the load resistor 144. As a result, the capacitor 143 and the load resistor 144 may adjust a time for which the rectified signal output to the cathode of the diode 142 is maintained, and may reconstruct the rectified signal into the low frequency baseband signal. The signal output to a first node ND_1 may be the reconstructed low frequency baseband signal.

The amplifying circuit 150 may amplify and output the reconstructed low frequency baseband signal. The amplifying circuit 150 may include at least one differential amplifier 151. For example, at least one capacitor may be connected in series to each of a positive input terminal and a negative input terminal of the differential amplifier 151, but the present disclosure is not limited thereto. For example, resistors connected between the power supply voltage VDD and the ground GND may be connected in parallel between the rear end of each capacitor and each input terminal of the amplifying circuit 150, but the present disclosure is not limited thereto.

The reconstructed low frequency baseband signal output to the first node ND_1 may be output to a second node ND_2 through a capacitor connected to the positive input terminal of the differential amplifier 151. The positive input terminal of the differential amplifier 151 may receive a signal output to the second node ND_2.

The negative input signal IN_N which the second reception signal IN_2 input to the virtual electrode 120 passes through the inductor 131 may be transmitted to a third node ND_3 as it is. Accordingly, the bias voltage applied by resistors between the voltage VDD connected to the negative input terminal and the ground GND may appear at the third node ND_3. The negative input terminal of the differential amplifier 151 may receive a signal output to the third node ND_3. The signal output to the third node ND_3 may be a voltage used as a reference for differential amplification.

The differential amplifier 151 may differentially amplify the signal of the second node ND_2 input to the positive input terminal and the signal of the third node ND_3 input to the negative input terminal, and may output the amplified signal to a fourth node ND_4.

Figure 2A:
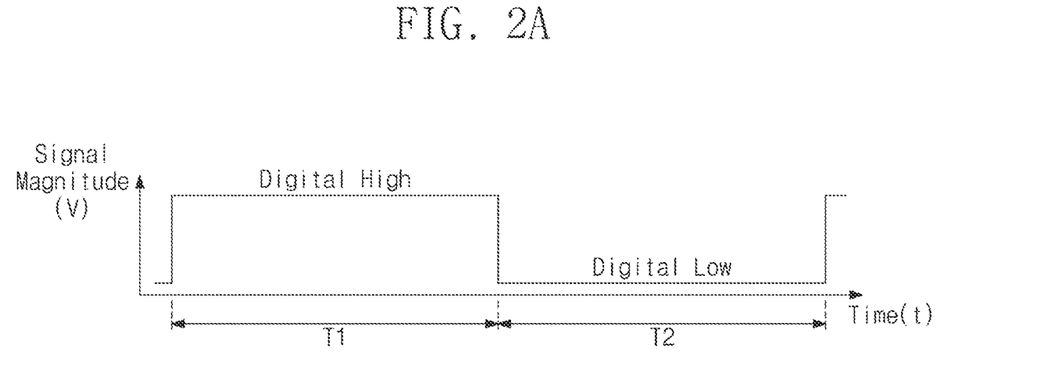
FIG. 2A is a diagram illustrating a waveform of a typical low frequency baseband signal.

FIG. 2A illustrates a waveform of a typical low frequency baseband signal. A time period T1 represents a period in which a signal value corresponds to digital high, and a time period T2 represents a period in which the signal value corresponds to digital low. For example, each of the time period T1 and the time period T2 may have a length of 10 μs.

As a transmission signal of human body communication, the low frequency baseband digital signal illustrated in FIG. 2A may be used as it is. However, when the frequency band of the transmission signal and the frequency band of noise are similar, the transmission signal and noise may overlap, the original transmission signal may be removed in a process of removing the noise, and recovery of the transmission signal may be impossible.

Figure 2B:
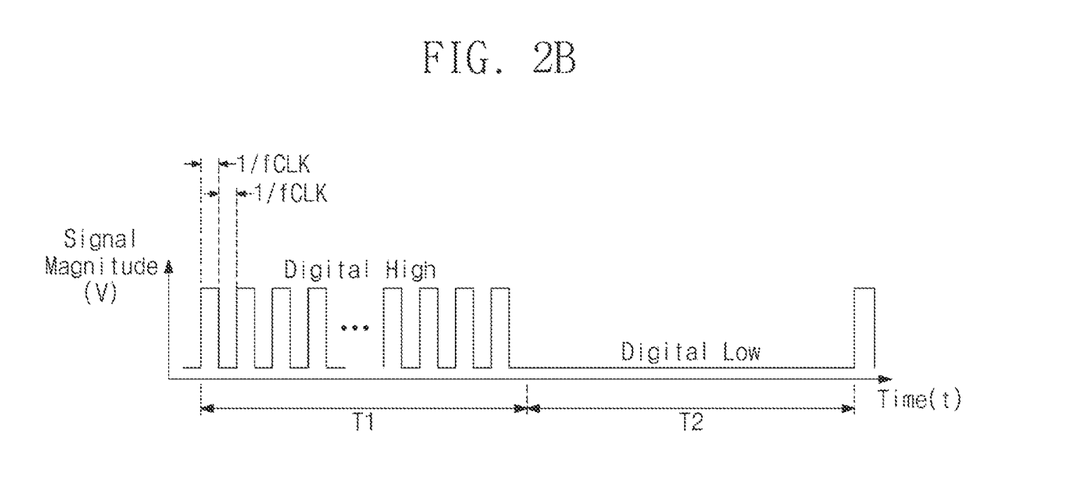
FIG. 2B is a diagram illustrating a waveform of a transmission signal according to an embodiment of the present disclosure.

FIG. 2B illustrates a waveform of a transmission signal according to an embodiment of the present disclosure. In the case of the time period T1, the human body signal transmitter (not illustrated) may map a high frequency pulse corresponding to the low frequency baseband signal illustrated in FIG. 2A. For example, when the length of the time period T1 is 10 μs, a high frequency pulse having a frequency fCLK of 10 MHz may be mapped with respect to the signal of the time period T1. In this case, the width (1/fCLK) of the mapped pulse may be 100 ns. In the case of the time period T2, as in FIG. 2A, the value of the signal may be maintained as a digital low for the same length of time as the time period T1.

When a signal obtained by mapping the high frequency pulse to the low frequency baseband signal as illustrated in FIG. 2B is used as the transmission signal of human body communication, the transmission signal and the low frequency noise may not overlap, and even in a process of removing the low frequency noise in the filter circuit 130 of FIG. 1, the original transmission signal may not be removed.

Figure 3:
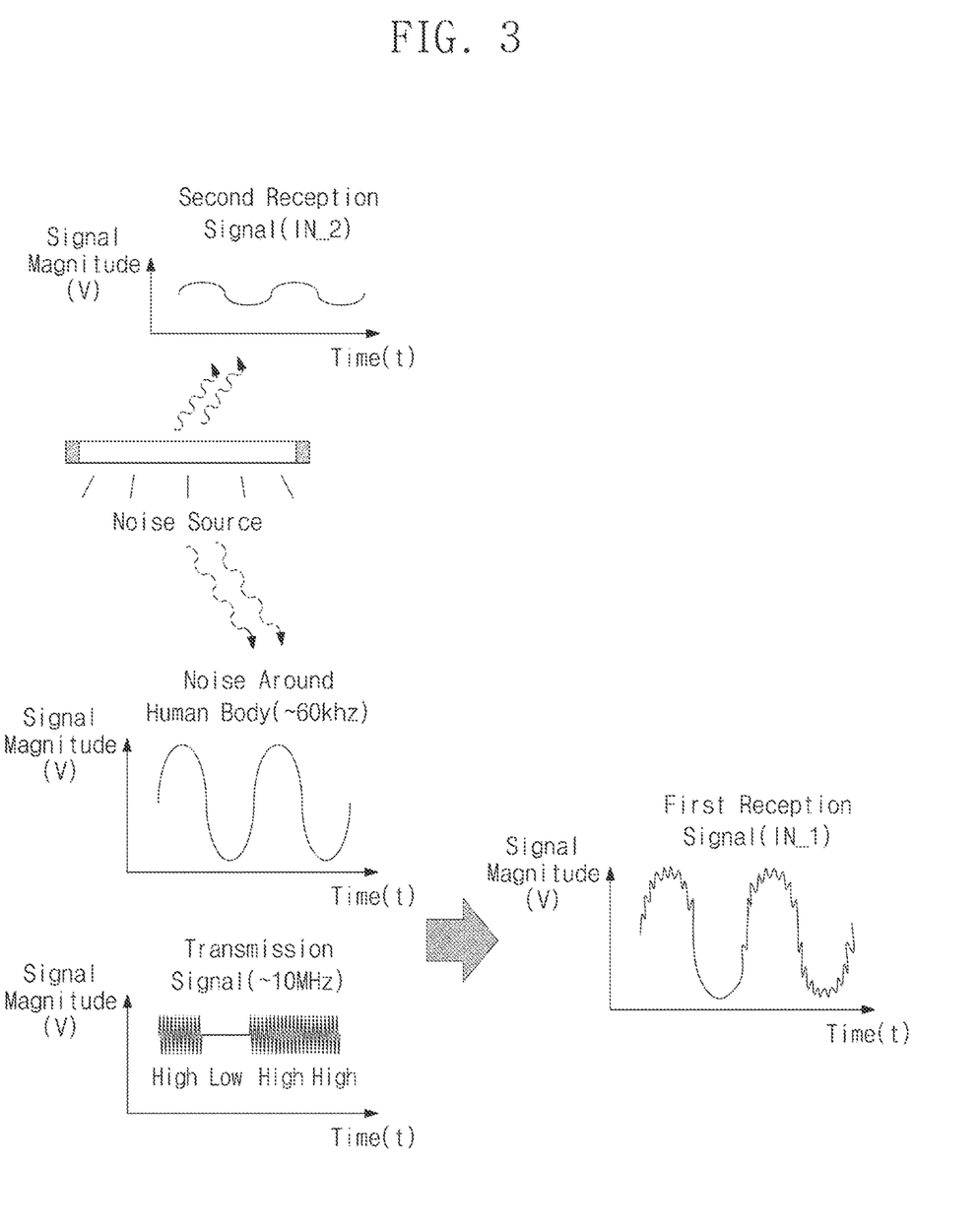
FIG. 3 is a diagram illustrating a waveform of a first reception signal input to a receiving electrode of FIG. 1 and a waveform of a second reception signal input to a virtual electrode of FIG. 1.

FIG. 3 illustrates a waveform of the first reception signal IN_1 input to the receiving electrode 110 of FIG. 1 and a waveform of the second reception signal IN_2 input to the virtual electrode 120 of FIG. 1. The first reception signal IN_1 and the second reception signal IN_2 may include noise introduced from the noise sources around the human body. For example, the noise source around the human body may be the fluorescent lamp, and the frequency of the noise may be 60 kHz.

The first reception signal IN_1 may be a signal in which the transmission signal and noise introduced from the noise sources around the human body are overlapped. For example, as described with reference to FIG. 2B, the transmission signal may be a signal including the high frequency pulse, and the frequency of the high frequency pulse may be 10 MHz.

The second reception signal IN_2 may be a signal in which an arbitrary reference voltage and noise introduced from the noise sources around the human body are overlapped. Unlike the first reception signal IN_1, the second reception signal IN_2 may not include the transmission signal, and thus may be the low frequency signal that does not include the high frequency pulse.

Figure 4A:
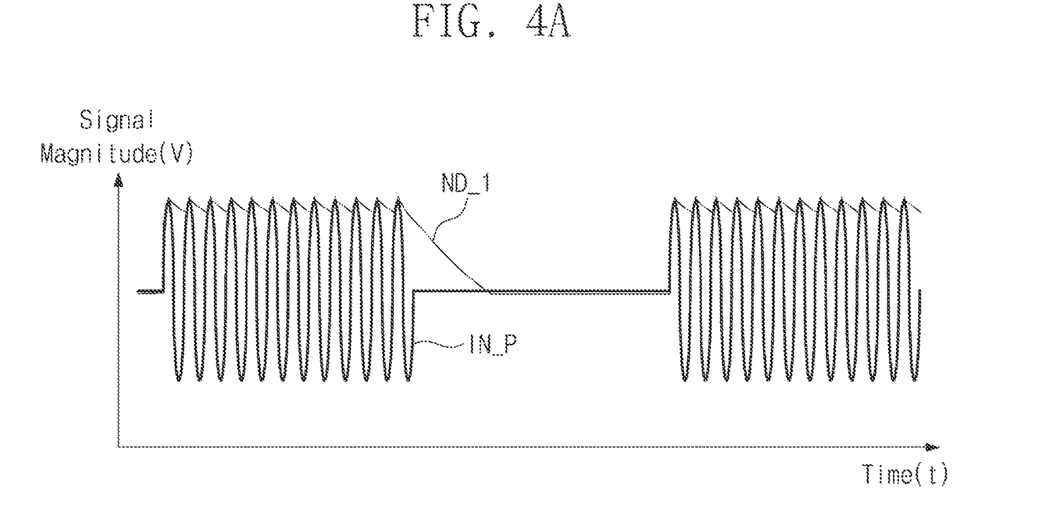
FIG. 4A is a diagram illustrating a waveform of a positive input signal of FIG. 1 and a waveform of a signal at the first node of FIG. 1.
Figure 4B:
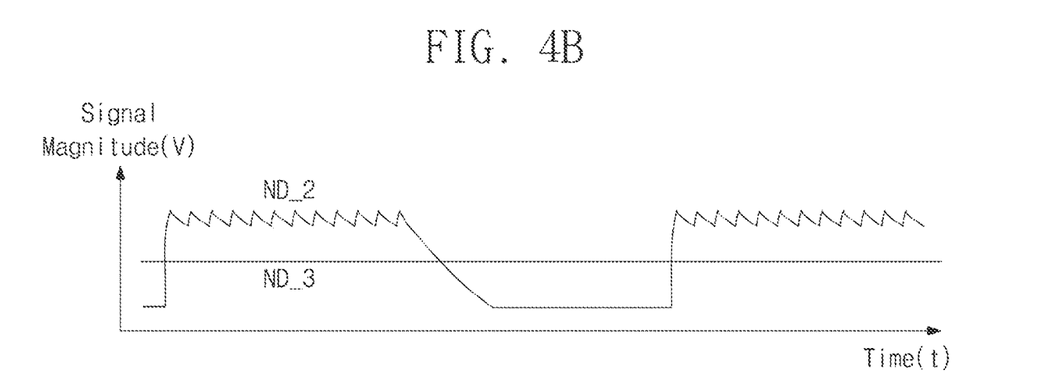
FIG. 4B is a diagram illustrating a waveforms of signals at a second node and a third node of FIG. 1.
Figure 4C:
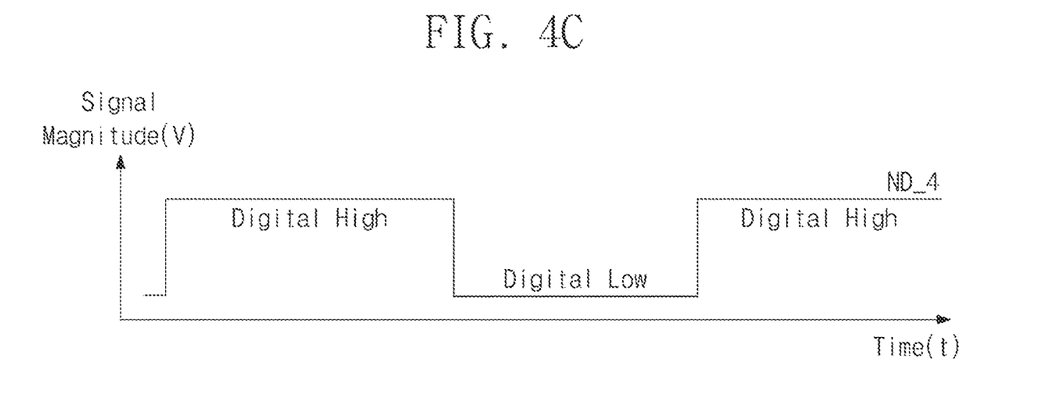
FIG. 4C is a diagram illustrating a waveform of a signal at a fourth node of FIG. 1.

FIG. 4A illustrates a waveform of the positive input signal IN_P of FIG. 1 and a waveform of a signal at the first node ND_1 of FIG. 1. FIG. 4B illustrates a waveforms of signals at the second node ND_2 and the third node ND_3 of FIG. 1. FIG. 4C illustrates a waveform of a signal at the fourth node ND_4 of FIG. 1. Hereinafter, it will be described with reference to FIG. 1 together with FIGS. 4A to 4C.

Referring to FIG. 4A, the positive input signal IN_P is a signal that passes through the capacitor 141 after the low frequency noise included in the first reception signal IN_1 is removed by the inductor 131, and a waveform of the positive input signal IN_P may be a form in which only the signal of the high frequency band remains in the waveform of the first reception signal IN_1 illustrated in FIG. 3.

The signal of the first node ND_1 is a reconstructed low frequency baseband signal including the rectified signal in which the positive input signal IN_P is rectified by the diode 142, and the waveform of the signal at the first node ND_1 may be a form in which the rectified signal is maintained and then discharged. The time during which the rectified signal included in the signal of the first node ND_1 is maintained may be adjusted by values of the capacitor 143 and the load resistor 144.

Referring to FIG. 4B, the signal of the second node ND_2 may be a signal in which the signal of the first node ND_1 passes through a capacitor connected to a front end of the positive input of the differential amplifier 151. The signal of the third node ND_3 may be a signal in which the negative input signal IN_N passes through a capacitor connected to a front end of the negative input of the differential amplifier 151.

Since the negative input signal IN_N is a signal having a magnitude close to zero as the inductor 131 removes the signal of the low frequency band from the second reception signal IN_2, the signal of the third node ND_3 may appear as a bias voltage applied by the resistors that are connected in parallel to a front end of the negative input of the differential amplifier 151 and are connected between the power supply voltage VDD and the ground GND. That is, as illustrated in FIG. 4B, waveforms of signals at the second node ND_2 and the third node ND_3 may appear based on the bias voltage. The signal of the second node ND_2 may be input to the positive input of the differential amplifier 151, and the signal of the third node ND_3 may be input to the negative input of the differential amplifier 151. The signal of the second node ND_2 may be amplified based on the magnitude of the signal of the third node ND_3.

Referring to FIG. 4C, the signal of the fourth node ND_4 may be a signal obtained by differentially amplifying the signal of the second node ND_2 and the signal of the third node ND_3 input to the differential amplifier 151. The waveform of a final signal at the fourth node ND_4 may appear as a waveform of the low frequency baseband signal before the high frequency pulse is mapped, as illustrated in FIG. 2A.

Figure 5:
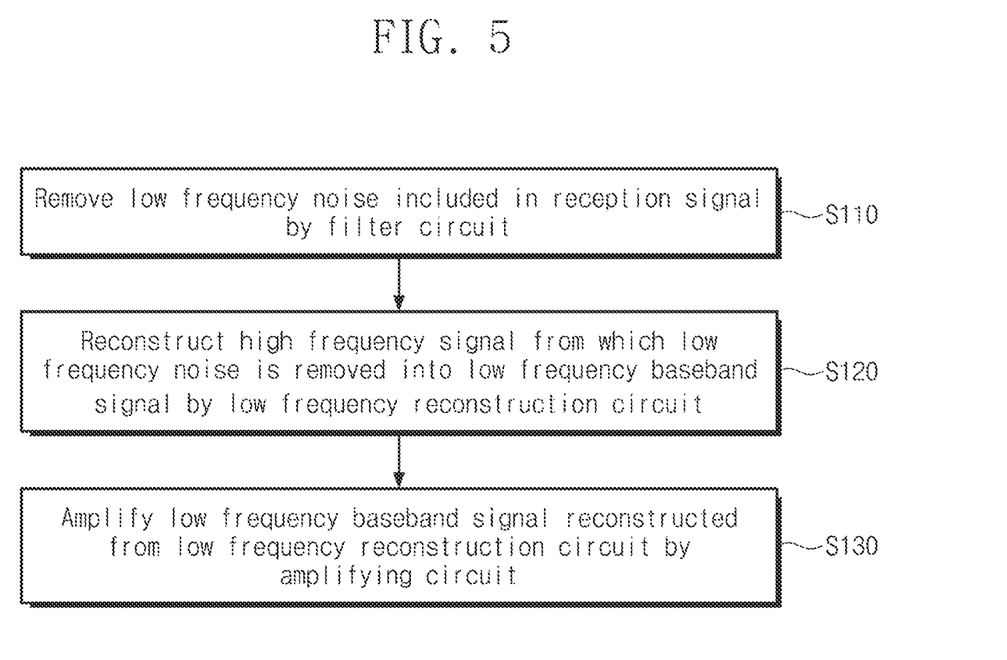
FIG. 5 is a flowchart illustrating a method of operating a human body communication receiver according to an embodiment of the present disclosure.

FIG. 5 is a flowchart illustrating a method of operating the human body communication receiver 100 according to an embodiment of the present disclosure. It will be described below with reference to FIG. 5 and FIG. 1.

In operation S110, the filter circuit 130 may remove low frequency noise included in the first reception signal IN_1. In operation S120, the low frequency reconstruction circuit 140 may reconstruct the high frequency signal from which the low frequency noise is removed into the low frequency baseband signal. In operation S130, the amplifying circuit 150 may amplify the low frequency baseband signal reconstructed by the low frequency reconstruction circuit 140.

Figure 6:
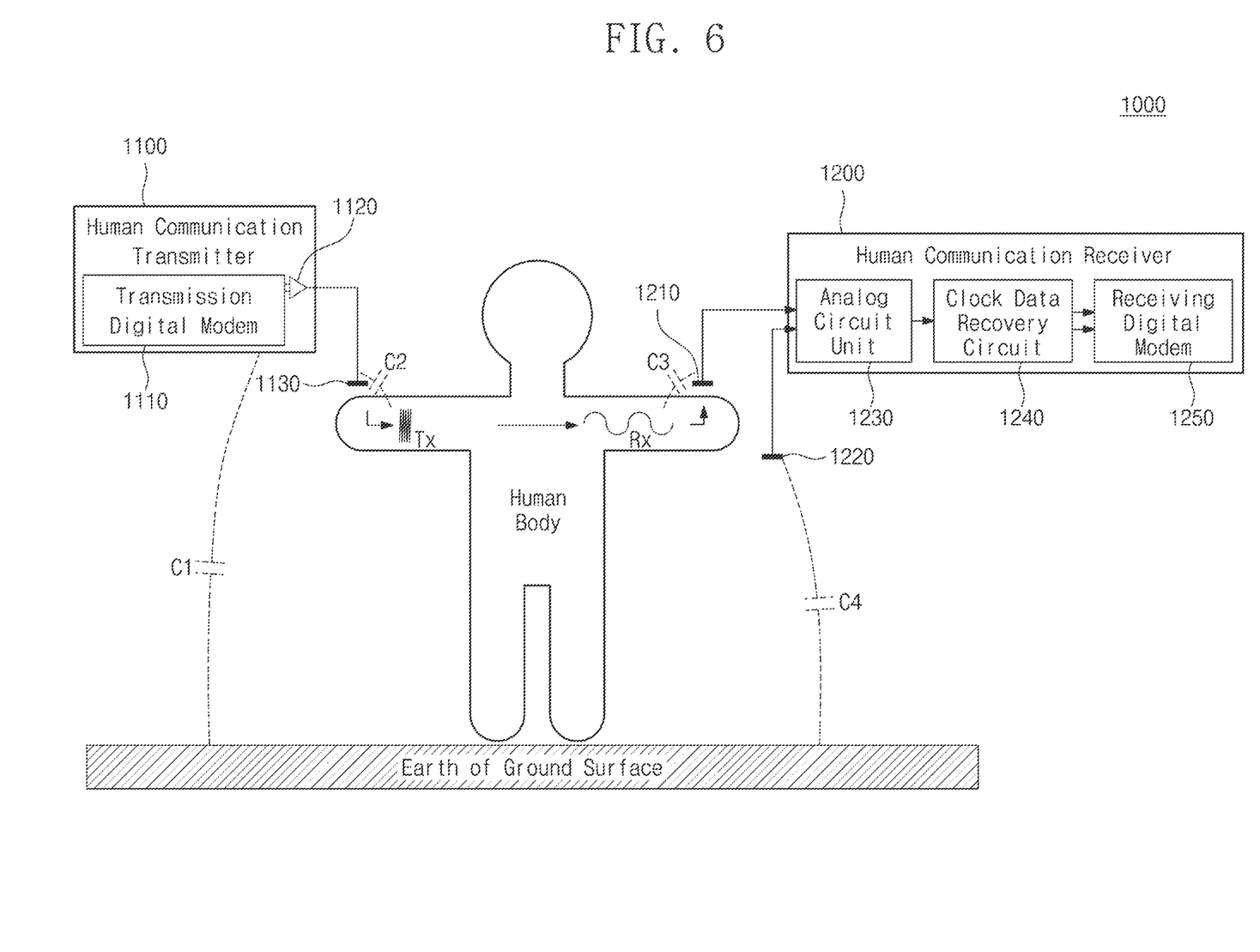
FIG. 6 is a diagram illustrating an apparatus for human body communication according to an embodiment of the present disclosure.

FIG. 6 is a diagram illustrating an apparatus 1000 for human body communication according to an embodiment of the present disclosure. The apparatus 1000 for human body communication may include a human body communication transmitter 1100 and a human body communication receiver 1200.

The human body communication transmitter 1100 may include a transmission digital modem 1110, a transmission electrode driving circuit 1120, and a transmission electrode 1130. The human body communication transmitter 1100 may transmit a transmission signal Tx to the human body, based on an electric field formed between the ground of the human body communication transmitter 1100 and earth of ground surface, and an electric field formed between the human body and the transmission electrode 1130.

For example, when a voltage that changes over time is applied to the transmission electrode 1130, an electric field that changes over time may be formed between the human body and the transmission electrode 1130, and charges that change over time in the human body may occur. Accordingly, the human body communication transmitter 1100 may transmit the transmission signal Tx to the human body. For example, a strength of each electric field described above may vary based on a capacitance C1 between the ground of the human body communication transmitter 1100 and the earth of ground surface, and a capacitance C2 between the human body and the transmission electrode 1130.

The transmission digital modem 1110 may generate transmission data based on a clock signal generated from a clock generator (not illustrated). The transmission electrode driving circuit 1120 may receive the transmission data generated by the transmission digital modem 1110 and may output the received transmission data to the transmission electrode 1130. The transmission electrode 1130 may transmit the transmission signal Tx to the human body. For example, the transmission electrode 1130 may be directly attached to the epidermis of the human body. For example, the transmission signal Tx may be the same as the transmission signal illustrated in FIG. 2B.

The human body communication receiver 1200 may include a receiving electrode 1210, a virtual electrode 1220, an analog circuit unit 1230, a clock data recovery circuit 1240, and a receiving digital modem 1250. The human body communication receiver 1200 may receive a reception signal Rx based on an electric field formed between the ground of the human body communication receiver 1200 and the earth of ground surface, and an electric field formed between the human body and the receiving electrode 1210.

For example, the charges that change over time generated in the human body may form the electric field that changes over time between the human body and the receiving electrode 1210. Accordingly, a voltage that changes over time may be applied to the receiving electrode 1210, and the reception signal Rx may be transmitted from the human body to the human body communication receiver 1200. For example, the strength of each electric field described above may vary based on a capacitance C3 between the human body and the receiving electrode 1210 and a capacitance C4 between the ground of the human body communication receiver 1200 and the earth of ground surface.

The receiving electrode 1210 may receive the reception signal Rx. For example, the receiving electrode 1210 may be directly attached to the epidermis of the human body. For example, the reception signal Rx may include noise introduced from noise sources around the human body. The virtual electrode 1220 may provide a voltage required for amplifying the reception signal Rx. For example, the virtual electrode 1220 may not contact the epidermis of the human body.

The analog circuit unit 1230 may remove noise from the reception signal Rx, and may amplify the reception signal Rx from which noise is removed to an appropriate magnitude, and output the amplified reception signal Rx. For example, the analog circuit unit 1230 may include the filter circuit 130, the low frequency reconstruction circuit 140, and the amplifying circuit 150 of FIG. 1. The clock data recovery circuit 1240 may generate a signal reconstructed by extracting a clock from a signal output from the analog circuit unit 1230. The receiving digital modem 1250 may receive the reconstructed signal and may recover the transmission data generated by the transmission digital modem 1110.

According to an embodiment of the present disclosure, it is possible to remove unnecessary noise from information included in a received signal of human body communication.

Furthermore, according to an embodiment of the present disclosure, low frequency noise may be effectively avoided by reconstructing a high frequency signal from which a noise signal is removed into an original low frequency baseband signal.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. A human body communication receiver comprising:
   a receiving electrode;
   a virtual electrode;
   a filter circuit connected between the receiving electrode and the virtual electrode, and configured to remove low frequency noise from a signal received through the receiving electrode to generate a high frequency signal;
   a low frequency reconstruction circuit connected to a rear end of the filter circuit, and configured to reconstruct a low frequency baseband signal by rectifying the high frequency signal; and
   an amplifying circuit connected to a rear end of the low frequency reconstruction circuit, and configured to amplify the low frequency baseband signal.

2. The human body communication receiver of claim 1, wherein the filter circuit includes at least one inductor.

3. The human body communication receiver of claim 1, wherein the low frequency reconstruction circuit includes:
   a diode;
   a first capacitor connected between an anode of the diode and the receiving electrode;
   a second capacitor connected between a cathode of the diode and the virtual electrode;
   a load resistor connected between the cathode of the diode and the virtual electrode; and
   a first plurality of resistors connected between the first capacitor and the anode of the diode.

4. The human body communication receiver of claim 3, wherein the first plurality of resistors are connected between a power supply voltage and a ground, and provide a first bias voltage to the anode of the diode.

5. The human body communication receiver of claim 1, wherein the amplifying circuit includes:
   a differential amplifier;
   a third capacitor connected between the rear end of the low frequency reconstruction circuit and a first input terminal of the differential amplifier;
   a fourth capacitor connected between the rear end of the low frequency reconstruction circuit and a second input terminal of the differential amplifier;
   a second plurality of resistors connected to the first input terminal; and
   a third plurality of resistors connected to the second input terminal.

6. The human body communication receiver of claim 5, wherein the second plurality of resistors and the third plurality of resistors are connected between a power supply voltage and a ground,
   wherein the second plurality of resistors provide a second bias voltage to the first input terminal of the differential amplifier, and wherein the third plurality of resistors provide a third bias voltage to the second input terminal of the differential amplifier.

7. The human body communication receiver of claim 5, wherein the first input terminal of the differential amplifier receives a first signal passed through the third capacitor connected to the first input terminal, wherein the second input terminal of the differential amplifier receives a second signal passed through the fourth capacitor connected to the second input terminal, and wherein the differential amplifier differentially amplifies the first signal and the second signal.

8. An operating method of the human body communication receiver, the method comprising:

removing, by a filter circuit connected between a receiving electrode and a virtual electrode, low frequency noise from a signal received through the receiving electrode;

reconstructing, by a low frequency reconstruction circuit connected to a rear end of the filter circuit, a low frequency baseband signal by rectifying the high frequency signal; and amplifying, by an amplifying circuit connected to a rear end of the low frequency reconstruction circuit, the low frequency baseband signal.

9. The method of claim 8, wherein the low frequency reconstruction circuit includes:

a diode;

a first capacitor connected between an anode of the diode and the receiving electrode;

a second capacitor connected between a cathode of the diode and the virtual electrode;

a load resistor connected between the cathode of the diode and the virtual electrode; and a first plurality of resistors connected between the first capacitor and the anode of the diode.

10. The method of claim 9, wherein the reconstructing of the low frequency baseband signal includes:

generating, by the diode, a rectified signal by rectifying the high frequency signal;

storing the rectified signal in the second capacitor; and discharging, by the load resistor, the stored rectified signal.

11. The method of claim 10, wherein the first plurality of resistors are connected between a power supply voltage and a ground, and wherein the reconstructing of the low frequency baseband signal further includes providing, by the first plurality of resistors, a first bias voltage to the anode of the diode, before the generating of the rectified signal.

12. The method of claim 8, wherein the amplifying circuit includes:

a differential amplifier;

a third capacitor connected between the rear end of the low frequency reconstruction circuit and a first input terminal of the differential amplifier;

a fourth capacitor connected between the rear end of the low frequency reconstruction circuit and a second input terminal of the differential amplifier;

a second plurality of resistors connected to the first input terminal; and a third plurality of resistors connected to the second input terminal.

13. The method of claim 12, wherein the second plurality of resistors and the third plurality of resistors are connected between a power supply voltage and a ground, and wherein the amplifying of the low frequency baseband signal includes:

providing, by the second plurality of resistors, a second bias voltage to the first input terminal of the differential amplifier; and providing, by the third plurality of resistors, a third bias voltage to the second input terminal of the differential amplifier.

14. The method of claim 12, wherein the amplifying of the low frequency baseband signal includes:

receiving, by the first input terminal of the differential amplifier, a first signal passing through the third capacitor connected to the first input terminal;

receiving, by the second input terminal of the differential amplifier, a second signal passing through the fourth capacitor connected to the second input terminal; and differentially amplifying, by the differential amplifier, the first signal and the second signal.

\* \* \* \* \*